United States Patent
Latham

(10) Patent No.: US 11,585,801 B2
(45) Date of Patent: *Feb. 21, 2023

(54) DETERMINING THE AGE OF A TUNNEL

(71) Applicant: The MITRE Corporation, McLean, VA (US)

(72) Inventor: Robert Latham, Springfield, VA (US)

(73) Assignee: The MITRE Corporation, McLean, VA (US)

( * ) Notice: Subject to any disclaimer, the term of this patent is extended or adjusted under 35 U.S.C. 154(b) by 476 days.

This patent is subject to a terminal disclaimer.

(21) Appl. No.: 16/913,762

(22) Filed: Jun. 26, 2020

(65) Prior Publication Data
US 2020/0340969 A1    Oct. 29, 2020

Related U.S. Application Data

(63) Continuation of application No. 15/973,166, filed on May 7, 2018, now Pat. No. 10,697,952.

(51) Int. Cl.
*G01N 33/24*    (2006.01)
*G01N 23/207*   (2018.01)
(Continued)

(52) U.S. Cl.
CPC ......... *G01N 33/24* (2013.01); *G01N 21/3563* (2013.01); *G01N 21/79* (2013.01);
(Continued)

(58) Field of Classification Search
CPC ....... G01N 2021/3572; G01N 21/3563; G01N 21/79; G01N 23/2076; G01N 23/223; G01N 33/24
See application file for complete search history.

(56) References Cited

U.S. PATENT DOCUMENTS 9,261,492 B2    2/2016 Lee et al.
9,470,665 B2 * 10/2016 Eisenhauer ............ G01N 30/06
(Continued)

FOREIGN PATENT DOCUMENTS

CN    205538315 U    8/2016

OTHER PUBLICATIONS

Blasco-Lopez, F. J. et al. (2015) "Methodology for characterising microlayers in historical piasterwork," Construction and Building Materials 93, pp. 463-470.
(Continued)

*Primary Examiner* — Jennifer Wecker
(74) *Attorney, Agent, or Firm* — Morrison & Foerster LLP

(57) ABSTRACT

Method, systems, and techniques for determining the age of an underground space are provided. In some embodiments, determining the age of an underground space comprises taking soil samples from a plurality of surface locations within a second underground space, analyzing the soil samples from the plurality of surface locations to determine an amount of a chemical compound for each soil sample, and determining an age of the second underground space using one or more relationships based on amounts of the chemical compound measured in a plurality of soil samples taken over a period of time in a first underground space and a baseline amount of the chemical compound at one or more locations remote from both the first underground space and the second underground space.

21 Claims, 7 Drawing Sheets

(51) Int. Cl.
 *G01N 21/3563* (2014.01)
 *G01N 21/79* (2006.01)
 *G01N 23/223* (2006.01)
(52) U.S. Cl.
 CPC ....... *G01N 23/2076* (2013.01); *G01N 23/223* (2013.01); *G01N 2021/3572* (2013.01)

(56) References Cited

U.S. PATENT DOCUMENTS

2015/0334914 A1* 11/2015 Zielke .................... A01B 27/00
 701/50
2016/0313271 A1* 10/2016 Raupach .............. G01N 27/048

OTHER PUBLICATIONS

Frumkin, Amos et al. (2006) "Tunnel engineering in the Iron Age: geoarchaeology of the Siloam Tunnel, Jerusalem," Journal of Archaeological Science 33, pp. 227-237.
Viscarra Rossel, R.A. et al. (2016) "Baseline estimates of soil organic carbon by proximal sensing: Comparing design-based, model-assisted and model-based inference," Geoderma 265, pp. 152-163.
Walker, M. (2005) "Some problematic dating materials," Section 5, Chapter 2—Radiometric Dating 1: Radiocarbon Dating, Quaternary Dating Methods, pp. 29-32.
Xing, Chengqi et al. (2002) "Thickness of calcium carbonate coats on stones of the Heishanxia terraces of the Yellow River and dating of coarse clastic sedimentary geomorphic surfaces," Chinese Science Bulletin, vol. 47, No. 19, pp. 1594-1595.

* cited by examiner

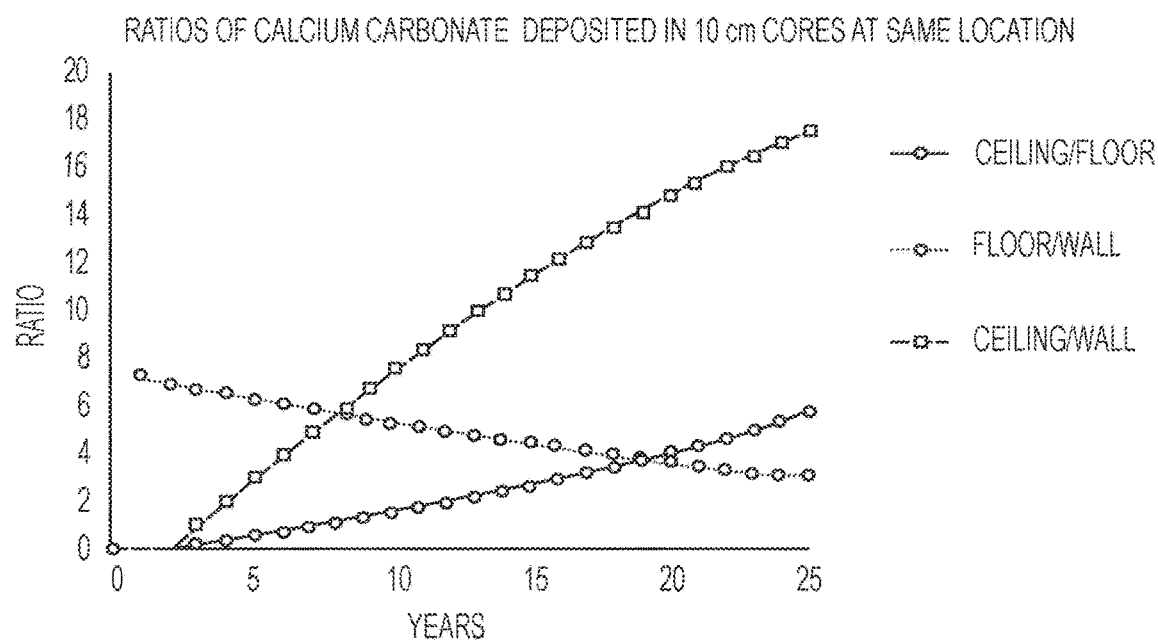
FIG. 3
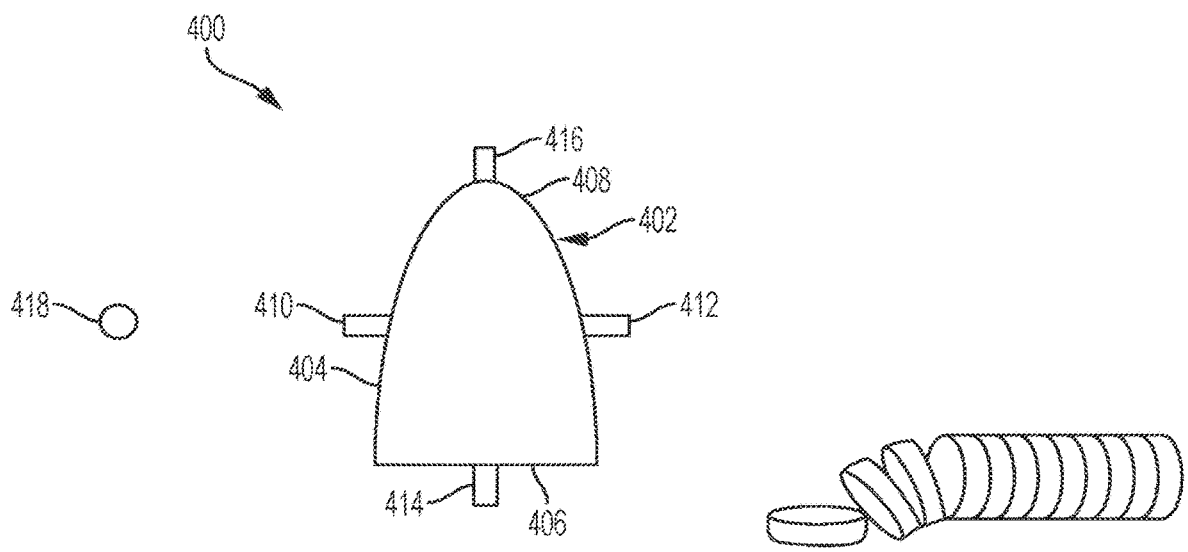
FIG. 4A
FIG. 4B

DETERMINING THE AGE OF A TUNNEL

CROSS-REFERENCE TO RELATED APPLICATIONS

This application is a continuation of U.S. application Ser. No. 15/973,166, filed May 7, 2018, the entire contents of which is incorporated herein by reference.

STATEMENT REGARDING FEDERALLY SPONSORED RESEARCH OR DEVELOPMENT

This invention was made with Government support under U.S. Government contract HSHQDC-16-J-00096, awarded by the U.S. Department of Homeland Security. The Government has certain rights in this invention.

FIELD OF THE INVENTION

This relates to methods for determining the age of underground spaces, and, particularly, to determining the age of underground spaces based on soil samples.

BACKGROUND OF THE INVENTION

Underground spaces are used for a variety of purposes. For example, an underground tunnel may be used for military purposes, for transportation, for utility/water supplies, and/or for smuggling contraband such as weapons, drugs, or even people. Many tunnels are located along the southwest border of the United States and are used for drug trafficking.

It is often desirable to know when an underground space was created. For example, when law enforcement discovers a drug trafficking tunnel and shuts it down, it is useful to know who owned and occupied the land when the tunnel was constructed. Accordingly, there is a need for improved systems, methods, and techniques for determining the age of a tunnel.

SUMMARY OF THE INVENTION

Described are systems and methods for determining the age of an underground space such as a tunnel. These systems and methods include taking soil samples from the underground space, analyzing the soil samples to determine an amount of a chemical compound in each soil sample, and determining the age of the underground space based on the amount of chemical compound and one or more relationships that are based on amounts of the chemical compound measured in a plurality of soil samples taken over a period of time. One or more relationships based on amounts of the chemical compound measured in a plurality of soil samples taken over a period of time may be determined by taking soil samples from a plurality of surface locations within a separate underground space at two or more time periods and analyzing the soil samples to determine a plurality of amounts of the chemical compound.

A method for determining the age of a tunnel can help a user identify those who owned and/or occupied the land under which the underground space was constructed. For example, samples of soil located around an underground space may be taken. In some embodiments, an amount of a chemical compound may be determined, which can then be applied to relationships based on the concentration of the chemical compound, times, and location relative to a surface of the underground space to determine the age of the underground space. Additionally, disclosed methods may also help users determine the age of military tunnels, underground storage facilities, hiding locations, unearthed communities, and/or manmade structures. Thus, described herein are methods that may address one or more of the issues described above.

In some embodiments, a method for determining the age of an underground space is provided, the method comprising: taking soil samples from a plurality of surface locations within a first underground space at two or more known periods of time; analyzing the soil samples from the plurality of surface locations within the first underground space at the two or more known periods of time to determine an amount of a chemical compound in each of the soil samples from the plurality of surface locations within the first underground space at the two or more known periods of time; determining one or more relationships between the first amount of the chemical compound in the soil samples from the plurality of surface locations within the first underground space at the two or more known periods of time; taking soil samples from a plurality of surface locations within a second underground space; analyzing the soil samples from the plurality of surface locations within the second underground space to determine an amount of the chemical compound in each of the soil samples from the plurality of surface locations within the second underground space; and determining an age of the second underground space based on the one or more relationships and the amount of the chemical compound from each of the soil samples from the plurality of surface locations within the second underground space.

In some embodiments of the method for determining the age of a tunnel, the two or more known periods of time are one year or more apart.

In some embodiments of the method for determining the age of a tunnel, the method further comprises analyzing a soil sample from one or more locations remote from the first underground space.

In some embodiments of the method for determining the age of a tunnel, the method further comprises analyzing a soil sample from one or more locations remote from the second underground space.

In some embodiments of the method for determining the age of a tunnel, the plurality of surface locations comprises two or more of a wall surface location, a floor surface location, and a ceiling surface location.

In some embodiments of the method for determining the age of a tunnel, the soil samples from the plurality of surface locations within the first underground space comprise at least one sample from each of a wall surface location, a floor surface location, and a ceiling surface location of the first underground space.

In some embodiments of the method for determining the age of a tunnel, the soil samples from the plurality of surface locations within the first underground space are each taken at a distance from an entrance of the first underground space.

In some embodiments of the method for determining the age of a tunnel, the soil samples from the plurality of surface locations within the second underground space comprise at least one sample from each of a wall surface location, a floor surface location, and a ceiling surface location of the second underground space.

In some embodiments of the method for determining the age of a tunnel, the soil samples from the plurality of surface locations within the second underground space are each taken at a distance from an entrance of the second underground space.

In some embodiments of the method for determining the age of a tunnel, analyzing the soil samples from the plurality of surface locations within the second underground space comprises: slicing a soil sample from a surface location of the plurality of surface locations into a plurality of sample slices, wherein each sample slice of the plurality of sample slices has a width of 0.5 inches to 1.5 inches and represents a different distance from the surface location of the plurality of surface locations; grinding each sample slice of the plurality of sample slices individually to a powder; and analyzing individual powder samples to determine an amount of the chemical compound in each sample slice of the plurality of sample slices of the soil sample.

In some embodiments of the method for determining the age of a tunnel, analyzing the individual powder samples to determine an amount of the chemical compound comprises one or more of x-ray diffraction, chemical infrared spectroscopy, x-ray fluorescence, or chemical titration.

In some embodiments of the method for determining the age of a tunnel, the age of the second underground space is 2 years or more.

In some embodiments of the method for determining the age of a tunnel, the age of the second underground space is 25 years or less.

In some embodiments of the method for determining the age of a tunnel, both the first underground space and the second underground space are tunnels, wherein each tunnel comprises a width of 0.5 to 2 meters.

In some embodiments of the method for determining the age of a tunnel, the first underground space and the second underground space are both symmetric from a front view perspective.

In some embodiments of the method for determining the age of a tunnel, the soil samples from the plurality of surface locations within the first underground space and the soil samples from the plurality of surface locations within the second underground space each comprise a three-dimensional shape.

In some embodiments of the method for determining the age of a tunnel, the chemical compound comprises calcium carbonate, iron oxide, or asphalt.

In some embodiments of the method for determining the age of a tunnel, determining an age of the second underground space comprises using one or more ratios of a first amount of the chemical compound in a soil sample from one surface location of the plurality of surface locations within the second underground space to a second amount of the chemical compound in a soil sample from a second surface location of the plurality of surface locations within the second underground space.

In some embodiments of the method for determining the age of a tunnel, determining an age of the second underground space further comprises using one or more ratios of the second amount of the chemical compound in the soil sample from the second surface location of the plurality of surface locations within the second underground space to a third amount of the chemical compound in a soil sample from a third surface location of the plurality of surface locations within the second underground space.

In some embodiments, a method for determining the age of an underground space is provided, the method comprising: taking soil samples from a plurality of surface locations within a second underground space; analyzing the soil samples from the plurality of surface locations to determine an amount of a chemical compound in each of the soil samples from the plurality of surface locations; and determining an age of the second underground space using one or more relationships based on amounts of the chemical compound measured in a plurality of soil samples taken over a period of time from a first underground space and a baseline amount of the chemical compound at one or more locations remote from both the first underground space and the second underground space.

In some embodiments of the method for determining the age of a tunnel, the method further comprises analyzing a soil sample from one or more locations remote from the second underground space.

In some embodiments of the method for determining the age of a tunnel, the plurality of surface locations comprises two or more of a wall surface location, a floor surface location, and a ceiling surface location.

In some embodiments of the method for determining the age of a tunnel, the soil samples from the plurality of surface locations within the second underground space comprise at least one sample from each of a wall surface location, a floor surface location, and a ceiling surface location of the underground space.

In some embodiments of the method for determining the age of a tunnel, the soil samples from the plurality of surface locations within the second underground space are each taken at a distance from an entrance of the second underground space.

In some embodiments of the method for determining the age of a tunnel, analyzing the soil samples comprises: slicing a soil sample from a surface location of the plurality of surface locations into a plurality of sample slices, wherein each sample slice of the plurality of sample slices has a width of 0.5 inches to 1.5 inches and represents a different distance from the surface location of the plurality of surface locations; grinding each sample slice of the plurality of sample slices individually to a powder; analyzing individual powder samples to determine an amount of the chemical compound in each sample slice of the plurality of sample slices of the soil sample.

In some embodiments of the method for determining the age of a tunnel, analyzing the individual powder samples to determine an amount of the chemical compound comprises one or more of x-ray diffraction, chemical infrared spectroscopy, x-ray fluorescence, or chemical titration.

In some embodiments of the method for determining the age of a tunnel, the age of the second underground space is 2 years or more.

In some embodiments of the method for determining the age of a tunnel, the age of the second underground space is 25 years or less.

In some embodiments of the method for determining the age of a tunnel, both the first underground space and the second underground space are tunnels each comprising a width of 0.5 to 2 meters.

In some embodiments of the method for determining the age of a tunnel, the first underground space and the second underground space are both symmetric from a front view perspective.

In some embodiments of the method for determining the age of a tunnel, the soil samples from the plurality of surface locations within the second underground space each comprise a three-dimensional shape.

In some embodiments of the method for determining the age of a tunnel, the chemical compound is calcium carbonate, iron oxide, or asphalt.

In some embodiments of the method for determining the age of a tunnel, determining an age of the second underground space comprises using one or more ratios of a first amount of the chemical compound in a soil sample from a first surface location of the plurality of surface locations to a second amount of the chemical compound in a soil sample from a second surface location of the plurality of surface locations.

In some embodiments of the method for determining the age of a tunnel, determining an age of the second underground space further comprises using one or more ratios of the second amount of the chemical compound in the sample from the second surface location of the plurality of surface locations to a third amount of the chemical compound in a sample from a third surface location of the plurality of surface locations.

In some embodiments, a method for determining an age of an underground space is provided, the method comprising: taking soil samples from a plurality of surface locations within an underground space; determining an amount of a chemical compound in each of the soil samples from the plurality of surface locations within the underground space; determining an amount of the chemical compound at one or more locations remote from the underground space; and determining an age of the underground space based on the amount of the chemical compound in each of the soil samples from the plurality of surface locations relative to the amount of the chemical compound at the one or more locations remote from the underground space.

In some embodiments of the method for determining the age of a tunnel, the method further comprises subtracting the amount of the chemical compound determined at the remote location from the amount of chemical compound in the soil samples from the plurality of surface locations within the underground space.

In some embodiments of the method for determining the age of a tunnel, the plurality of surface locations comprises two or more of a wall surface location, a floor surface location, and a ceiling surface location.

In some embodiments of the method for determining the age of a tunnel, the soil samples comprise at least one sample from each of a wall surface location, a floor surface location, and a ceiling surface location.

In some embodiments of the method for determining the age of a tunnel, the soil samples are each taken at a same distance within the underground space relative to an entrance of the underground space.

In some embodiments of the method for determining the age of a tunnel, determining an amount of a chemical compound comprises: slicing a soil sample from a surface location of the plurality of surface locations into a plurality of sample slices, wherein each sample slice of the plurality of sample slices has a width of 0.5 inches to 1.5 inches and represents a different distance from the surface location of the plurality of surface locations; grinding each sample slice of the plurality of sample slices individually to a powder; and analyzing individual powder samples to determine an amount of the chemical compound in each sample slice of the plurality of sample slices of the soil sample.

In some embodiments of the method for determining the age of a tunnel, analyzing individual powder samples to determine an amount of the chemical compound comprises one or more of x-ray diffraction, chemical infrared spectroscopy, x-ray fluorescence, or chemical titration.

In some embodiments of the method for determining the age of a tunnel, the age of the underground space is 2 years or more.

In some embodiments of the method for determining the age of a tunnel, the age of the underground space is 25 years or less.

In some embodiments of the method for determining the age of a tunnel, the underground space is a tunnel comprising a width of 0.5 to 2 meters.

In some embodiments of the method for determining the age of a tunnel, the underground space is symmetric from a front view perspective.

In some embodiments of the method for determining the age of a tunnel, the soil samples comprise a three-dimensional shape.

In some embodiments of the method for determining the age of a tunnel, the chemical compound is calcium carbonate, iron oxide, or asphalt.

In some embodiments of the method for determining the age of a tunnel, determining an age of the underground space based on the amount of chemical compound in the soil samples from the plurality of soil samples comprises using one or more ratios of a first amount of the chemical compound in a sample from a first surface location of the plurality of surface locations to a second amount of the chemical compound in a sample from a second surface location of the plurality of surface locations.

In some embodiments of the method for determining the age of a tunnel, determining an age of the underground space based on the amount of chemical compound in the soil samples from the plurality of soil samples further comprises using one or more ratios of the second amount of the chemical compound in the sample from the second surface location of the plurality of surface locations to a third amount of the chemical compound in a sample from a third surface location of the plurality of surface locations.

In some embodiments, a method for generating a model to determine the age of an underground space is provided, the method comprising: analyzing soil samples collected from a plurality of surface locations within an underground space at a first and a second known periods of time to determine an amount of a chemical compound in each of the soil samples from the plurality of surface locations within the underground space from the first and second known periods of time; and determining one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

In some embodiments of the method for generating a model to determine the age of an underground space, the first and the second known periods of time are one year or more apart.

In some embodiments of the method for generating a model to determine the age of an underground space, the method further comprises analyzing a soil sample from one or more locations remote from the underground space.

In some embodiments of the method for generating a model to determine the age of an underground space, the plurality of surface locations comprises two or more of a wall surface location, a floor surface location, and a ceiling surface location.

In some embodiments of the method for generating a model to determine the age of an underground space, analyzing the soil samples from the plurality of surface locations within the underground space comprises: receiving a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder; and analyzing each individual powder sample to determine amounts of the chemical compound in each sample slice of the plurality of sample slices of the soil sample.

In some embodiments of the method for generating a model to determine the age of an underground space, determining one or more relationships between the determined amounts of the chemical compound in the soil samples comprises determining one or more ratios of a first amount of the chemical compound in a soil sample from one surface location of the plurality of surface locations within the underground space to a second amount of the chemical compound in a soil sample from a second surface location of the plurality of surface locations within the underground space.

In some embodiments of the method for generating a model to determine the age of an underground space, determining one or more relationships between the determined amounts of the chemical compound in the soil samples further comprises determining one or more ratios of the second amount of the chemical compound in the soil sample from the second surface location of the plurality of surface locations within the underground space to a third amount of the chemical compound in a soil sample from a third surface location of the plurality of surface locations within the underground space.

In some embodiments, a system for generating a model to determine the age of an underground space is provided, the system comprising: a processor; and a memory storing instructions that, when executed by the processor, cause the processor to: analyze soil samples collected from a plurality of surface locations within an underground space at a first and a second known periods of time to determine an amount of a chemical compound in each of the soil samples from the plurality of surface locations within the underground space from the first and second known periods of time; and determine one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

In some embodiments of the system for generating a model to determine the age of an underground space, the first and the second known periods of time are one year or more apart.

In some embodiments of the system for generating a model to determine the age of an underground space, the instructions, when executed by the processor, further cause the processor to analyze a soil sample from one or more locations remote from the underground space.

In some embodiments of the system for generating a model to determine the age of an underground space, the plurality of surface locations comprises two or more of a wall surface location, a floor surface location, and a ceiling surface location.

In some embodiments of the system for generating a model to determine the age of an underground space, the instructions that cause the processor to analyze soil samples collected from a plurality of surface locations within the underground space comprise instructions that cause the processor to, when having received a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder, analyze each individual powder sample to determine amounts of the chemical compound in each sample slice of the plurality of sample slices of the soil sample.

In some embodiments of the system for generating a model to determine the age of an underground space, the instructions causing the processor to determine one or more relationships between the determined amounts of the chemical compound in the soil samples comprise instructions that cause the processor to determine one or more ratios of a first amount of the chemical compound in a soil sample from one surface location of the plurality of surface locations within the underground space to a second amount of the chemical compound in a soil sample from a second surface location of the plurality of surface locations within the underground space.

In some embodiments of the system for generating a model to determine the age of an underground space, the instructions that cause the processor to determine one or more relationships between the determined amounts of the chemical compound in the soil samples further comprises instructions that cause the processor to determine one or more ratios of the second amount of the chemical compound in the soil sample from the second surface location of the plurality of surface locations within the underground space to a third amount of the chemical compound in a soil sample from a third surface location of the plurality of surface locations within the underground space.

In some embodiments, a non-transitory computer readable storage medium storing instructions for generating a model to determine the age of an underground space is provided, the non-transitory computer readable storage medium comprising instructions that are executable by a system and a processor to cause the system to: analyze soil samples collected from a plurality of surface locations within an underground space at a first and second known periods of time to determine an amount of a chemical compound in each of the soil samples from the plurality of surface locations within the underground space; and determine one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

In some embodiments of the non-transitory computer readable storage medium, the first and second known periods of time are one year or more apart.

In some embodiments of the non-transitory computer readable storage medium, the instructions, when executed by the processor, further cause the processor to analyze a soil sample from one or more locations remote from the underground space.

In some embodiments of the non-transitory computer readable storage medium, the plurality of surface locations comprises two or more of a wall surface location, a floor surface location, and a ceiling surface location.

In some embodiments of the non-transitory computer readable storage medium, the instructions that cause the processor to analyze the soil samples from the plurality of surface locations within the underground space comprise instructions that further cause the processor to, when having receiving a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder, analyze each individual powder sample to determine amounts of the chemical compound in each sample slice of the plurality of sample slices of the soil sample.

In some embodiments of the non-transitory computer readable storage medium, the instructions that cause the processor to determine one or more relationships between the determined amounts of the chemical compound in the soil samples comprise instructions that further cause the processor to determine one or more ratios of a first amount of the chemical compound in a soil sample from one surface location of the plurality of surface locations within the underground space to a second amount of the chemical compound in a soil sample from a second surface location of the plurality of surface locations within the underground space.

In some embodiments of the non-transitory computer readable storage medium, the instructions that cause the processor to determine one or more relationships between the determined amounts of the chemical compound in the soil samples further comprise instructions that cause the processor to determine one or more ratios of the second amount of the chemical compound in the soil sample from the second surface location of the plurality of surface locations within the underground space to a third amount of the chemical compound in a soil sample from a third surface location of the plurality of surface locations within the underground space.

BRIEF DESCRIPTION OF THE DRAWINGS

The invention will now be described, by way of example only, with reference to the accompanying drawings, in which:

FIG. 3 is a graph of ratios of the calcium carbonate deposition rate equations;

FIG. 4A is a front view of a tunnel showing soil sampling locations according to some embodiments;

FIG. 4B shows a method of preparing a soil sample for analysis according to some embodiments;

DETAILED DESCRIPTION OF THE INVENTION

Described are exemplary embodiments of methods for determining the age of an underground space. Specifically, methods provided may allow a user to determine the age of an underground space based on amounts of one or more chemical compounds in soil located proximate to the underground space.

As described below, when an underground area is created, it can disturb the natural downward flow of water through the soil. This disturbance in the amount of water and/or air flowing to underground soil may affect the reactions and depositions of chemical compounds located within the soil. For example, chemical compounds such as calcium carbonate, carbon dioxide, iron oxide, and/or asphalt may each be affected by water. Thus, any disturbance in the flow of water to an area of soil may affect the amount of calcium carbonate, carbon dioxide, iron oxide, and/or asphalt in that area. By determining how these disturbances affect the soil proximate to the underground space and by analyzing soil samples to determine amounts of a chemical compound, the age of the underground space can be determined.

Various embodiments of methods of determining the age of an underground space are described below in detail with reference to the figures included herein.

The Watershed Effect and the Shadow Region

Underground construction can create a "watershed effect" and a "shadow region" in the natural downward flow of water in the soil. Specifically, the creation of an underground space, such as a tunnel, can disturb the downward flow patterns of water. These disturbances in the downward water flow patterns can affect the amounts of various chemical compounds in the area. Prior to underground construction, underground areas of permeable ground soil theoretically can receive an input of chemical compounds and elements transported by the natural downward flow of groundwater caused by gravity. Underground construction, however, disrupts the natural water flow pattern. Consequently, underground construction may create a "watershed effect" in the water flow patterns in soil above the ceiling and inside the walls of the underground space and a water flow "shadow region" beneath the floor of the underground space.

Figure 1:
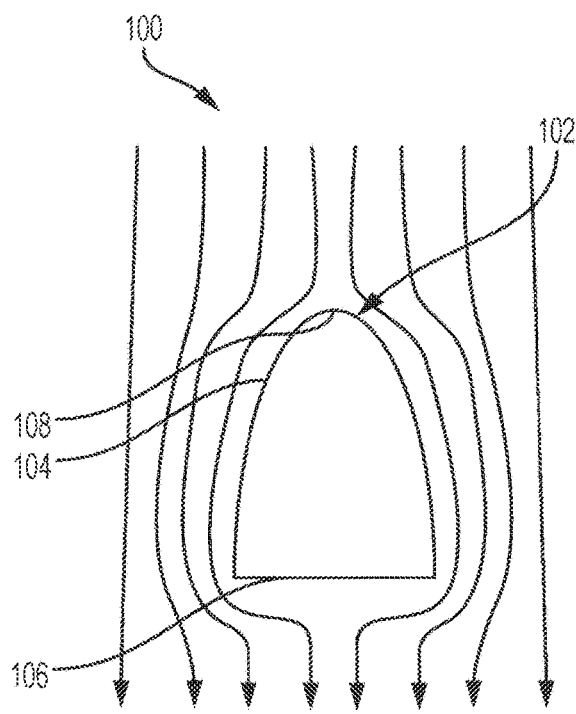
FIG. 1 shows a front view of an underground space showing water flow patterns around the underground space according to some embodiments.

A "watershed effect" is the result of changes in water flow including speed, direction and saturation in soil above the ceiling surface; a "shadow region" is the result of a reduction in water flowing to soil beneath the floor surface of an underground space. Both a "watershed effect" and a "shadow region" are depicted in FIG. 1. Specifically, FIG. 1 shows system 100 comprising tunnel 102 having ceiling surface location 108, wall surface location 104, and floor surface location 106. The arrows in the Figure indicate the water flow pattern around tunnel 102. The "watershed effect" includes the changes in water flow (including speed, direction and saturation) in soil above the ceiling surface location 108 and in soil beyond the wall surface locations 104. The "shadow region" is shown by the reduction of water flow to soil below floor surface location 106.

A "watershed effect" and a "shadow region" affect the soil in different surface locations (i.e., near a wall surface, a ceiling surface, and a floor surface) within an underground space in different ways. For example, in soil above ceiling surface location 108, water flow changes direction and so the flow can experience various reductions in speed at different points and at different times that can result in various saturation increases, also at different points and times. Initially, once the underground space is first constructed, some water may seep into the tunnel itself. However, depending on the soil parameters, soil surrounding the tunnel may become compressed and pores in the soil may fill causing a reduction or complete stoppage of water seepage into the tunnel. Instead, the water flow increases saturation in the soil above the ceiling surface location 108 of the underground space. The concentrations of chemical compounds in the water flowing to this area from above remain the same per unit volume of water. However, there is more water present within the pores of the soil located in the soil above the ceiling surface location 108 of the underground space. Thus, there are higher amounts of these compounds per bulk volume of soil, which may change the amount of chemical compound deposition per bulk volume.

Accumulation of compounds such as calcium carbonate is the combined result of both precipitation and dissolution occurring simultaneously depending on the available amounts of chemicals in the water (such as calcium ions and carbon dioxide for calcium carbonate). Because these are slow processes, the speed of water flow will also be a contributing factor. As such, the calcium carbonate accumulation rates in soil inside wall surface location 104 of an underground space are moderate compared to that of soil above the ceiling surface location 108 and below the floor surface location 106. The water that flows to soil near the ceiling surface location 108 of an underground space slows and diverges once it hits disturbed soil near the ceiling. In a symmetrical underground space, approximately half of the water approaching the ceiling surface location 108 will flow to a left wall and approximately half of the water will flow to a right wall. Accordingly, water saturation in soil around wall surface locations 104 of the underground space increases. However, the water that flows to the right and left wall surface locations 104 has already been depleted of some of its chemical compounds due to the chemical compound deposition at ceiling surface location 108 and due to relative increases in water flow speed in soil near the walls. Thus, this additional water saturation in soil near the wall surface locations 104 of the underground space only causes a moderate increase in chemical compound accumulation per bulk volume. Chemical compound deposition will be greater in soil closer to a wall surface location 104 of the underground space than further away from the wall surface, since carbon dioxide and other gases can more easily escape at the wall surfaces of the underground space (and thus increasing reaction rates of some chemical compounds). Because precipitation and dissolution of compounds such as calcium carbonate occur naturally in soils without tunnels, we may define a baseline value of compound accumulation as the amount of that compound that would have accumulated at a specific time and soil depth if the tunnel was not present. Any difference of chemical compound accumulation in soil near the wall surface locations 104, for example, relative to this baseline (excess or deficiency) can be related to the change in water flow and the fraction of the water diverted from the soil above the ceiling.

Additionally, at floor surface location 104, a "shadow region" is caused by a reduction of water flow. Because of the water flow patterns indicated by the arrows in FIG. 1, little, if any, water is able to reach the soil directly underneath a floor surface location 106 of the underground space. Accordingly, fewer additional chemical compounds are deposited in soil directly below the floor surface location 106 of an underground space, since there is no new water flowing to the area to bring new chemical compounds to form additional chemical compounds. Further, the original water located in this region prior to underground construction drains from this region. This drainage may cause continued chemical compound deposition for a short period of time, partially because there is more room in the pores for outgassing.

Various chemical compounds may be affected by water perturbations caused by a "watershed effect" and a "shadow region". For example, chemical compounds such as calcium carbonate, iron oxide, and/or asphalt may follow the described deposition patterns due to the "watershed effect" and the "shadow region" described above. In some embodiments, calcium carbonate in soil samples taken proximate to an underground space may be analyzed to determine the age of the underground space.

Calcium Carbonate in Soil

In some embodiments, concentrations of a chemical compound such as calcium carbonate may be measured in samples of soil taken from an underground space. Calcium carbonate is naturally precipitated and dissolved from the downward flow of calcium ions, carbonate ions, and carbon dioxide dissolved in water and is naturally present in soil in many geographic locations throughout the world. Specifically, calcium carbonate can be formed by the following chemical process:

$$Ca^{2+}+2HCO^-_3 \rightarrow CaCO_3+H^++HCO^-_3 \rightarrow CaCO_3+CO_2+H_2O$$

The overall calcium carbonate deposition rates (R) in water are determined predominantly by the concentration of calcium ions $[Ca^{2+}]$ and carbonate ions $[CO_3^{-2}]$:

$R =$ $R_{CG} + R_{HN}$ = total rate of calcium carbonate deposition $(\text{mol L}^{-1}\text{s}^{-1})$, where:

$R_{CG}$ = crystal growth deposition rate = $\kappa_f s \gamma_2^2 ([Ca^{2+}][CO_3^{-2}] - K_{sp}\gamma_2^{-2})$;

$R_{HN}$ = heterogeneous nucleation rate = $\kappa_{HN} f(s_p) \left( \left( \dfrac{[Ca^{2+}][CO_3^{-2}]}{K_{sp}} \right) - 2.5 \right)$;

$\kappa_f$ = crystal precipitation rate constant $(\approx 2.176e-10 \text{ mol}^{-1}\text{m}^{-2}\text{sec}^{-1})$;

$\kappa_{HN}$ = heterogenous precipitation rate constant;

$s$ = surface area calcium carbonate seeds $(\text{m}^2\text{L}^{-1})$;

$f(s_p)$ = functional change dependent on surface area of solution particles;

$\gamma_2$ = divalent ion activity coefficient; and $K_{sp}$ = solubility constant of calcium carbonate 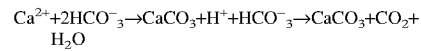 $(\approx 2.8 \times 10^{-9}$ in pure water, 25° C).

Under stable weather conditions, a fairly constant (or slowly increasing) concentration of calcium carbonate exists at any given depth below the ground surface, based on the difference between the precipitation rate and the dissolution rate. This stable calcium carbonate concentration, based on the steady precipitation and dissolution rates under normal conditions characteristic of a given geographic location, can determine a baseline value of calcium carbonate at a specific time and soil depth for that given geographic location.

However, as described above, underground construction can disturb the steady downward flow of water, creating a "watershed effect" and a "shadow region" in the downward flow of water surrounding the underground space. This disturbance in the natural water flow can affect the calcium carbonate deposition rates in the surrounding soil.

Characteristic calcium carbonate deposition profiles illustrating typical calcium carbonate deposition behavior in response to underground construction may be generated. Though optional, characteristic profiles of the calcium carbonate deposition may provide a first check to ensure that the soil samples will be useful and indicative of known calcium carbonate deposition patterns.

Figure 2:
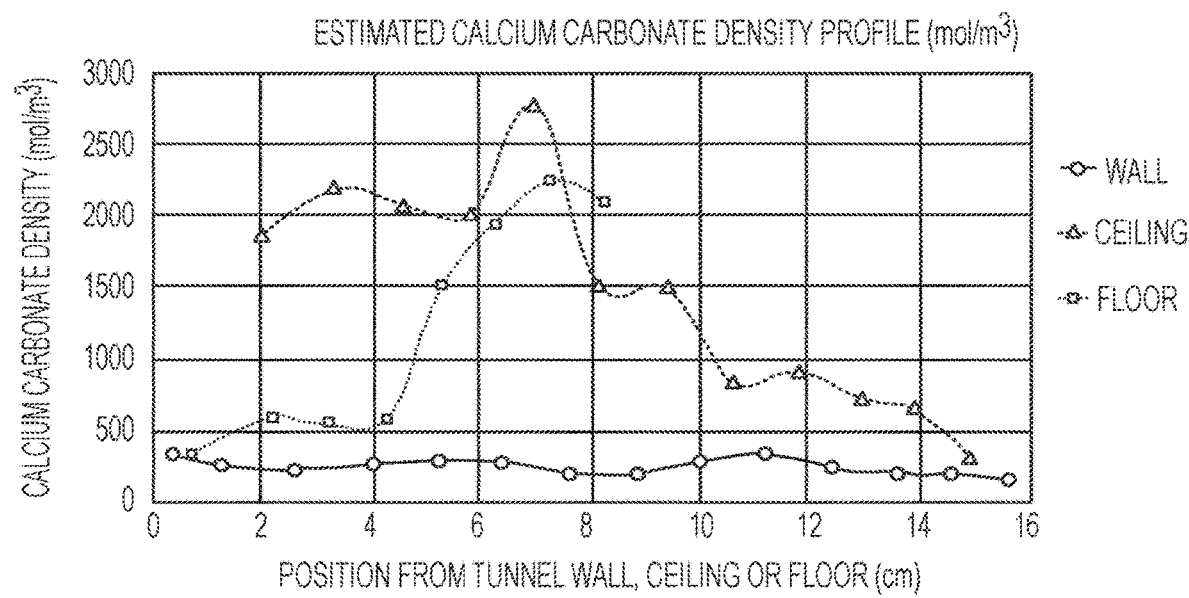
FIG. 2 is a graph of estimated calcium carbonate density profiles for samples obtained from three different surface locations within an underground space.

A characteristic calcium carbonate deposition profile may be generated for at least each of the three main surface locations around an underground space from which soil samples are obtained, shown in FIG. 2. To generate these profiles, soil samples can be obtained from various surface locations around the underground space, the soil samples can be analyzed to determine amounts of calcium carbonate in the soil samples, and the amounts of calcium carbonate can be used to generate characteristic calcium carbonate deposition profiles. In some embodiments, the calcium carbonate amounts may account for a baseline calcium carbonate value and be generally representative of the three main surface locations around any similarly-shaped underground surface regardless of geographic and/or geologic variables. In some embodiments, the characteristic calcium carbonate deposition profiles may be unique to that underground space, for example, by not accounting for a baseline calcium carbonate value of the underground space.

FIG. 2 shows characteristic calcium carbonate deposition profiles for each of a wall surface location, a floor surface location, and a ceiling surface location. Each of the deposition profiles in FIG. 2 have accounted for a baseline calcium carbonate value. Thus, each of the three deposition profiles may be generally representative of the calcium carbonate behavior of any underground space, regardless of how much calcium carbonate is naturally present in the surrounding soil. Generally, as indicated in the Figure, a wall profile will show the lowest overall calcium carbonate levels compared to the ceiling and floor data. Additionally, the wall profile (calcium carbonate level) is highest nearest the wall surface and decreases until it reaches the baseline calcium carbonate level, anywhere from 10 cm-30 cm into the soil. On the other hand, a floor profile typically exhibits low calcium carbonate levels closest to the floor surface and increases sharply to a calcium carbonate value that is higher than a calcium carbonate level ever reached in a wall profile. Finally, a typical ceiling profile shows the highest calcium carbonate level nearest the tunnel surface (compared to the floor and wall profiles), but at a depth of a few centimeters into the soil, the calcium carbonate level of the ceiling soil sample increases even further before steadily declining as the distance from the ceiling surface increases. Some variation is expected due to soil irregularities and available water and calcium.

Although the characteristic calcium carbonate deposition profile for each of the three surface locations (a wall surface location, a ceiling surface location, and a floor surface location) is different, they are all related. As described above, different surface locations around the underground space have different calcium carbonate deposition rates due to the different, yet dependent, water saturation levels. However, the surface locations of any given underground space share common parameters such as soil conductivity and initial water concentrations of calcium ions, carbonate ions, and dissolved carbon dioxide. Underground spaces with symmetric geometry (from a front view perspective) and uniform soil exhibit approximately equal amounts of ceiling water used to generate excess calcium carbonate in each of the walls (left and right). Further, the same amount of water that is in excess in the ceiling location (compared to an undisturbed underground location) is approximately the same amount of water missing from the floor location. Although the calcium carbonate deposition rate in soil at the various surface locations differs, the ratio of excess calcium carbonate in soil near a ceiling surface location of one underground space to that near a wall surface location of the same underground space at any given age is comparable to the same ratio in a second tunnel of the same age. (This same relationship applies to other ratios of calcium carbonate deposition. For example, the ratio of calcium carbonate deposition near a ceiling surface location to that near a floor surface location or the ratio of calcium carbonate deposition near a floor surface location to that near a wall surface location.) Accordingly, methods described herein may analyze the calcium carbonate deposition rates based on ratios of a calcium carbonate amount from one surface location to a calcium carbonate amount from another surface location to help account for any geographic and/or geologic variations between different underground spaces.

FIG. 3 shows the progressions of the various ratios between different surface locations for soil in the first 10 cm proximate to that surface. Because of the dependency of the calcium carbonate deposition rate near a wall surface location to that near a ceiling surface location (based on the watershed effect and the divergence of water flow from the ceiling between the left and right sides of the underground space), this relationship ratio is typically the strongest. The floor/wall and ceiling/floor deposition ratios are weaker because they compare a changing deposition rate (of the ceiling/wall) to the relatively constant deposition rate below the floor. Any outlier values may be excluded.

Modelling an Age of an Underground Space

As described below, the age of an underground space may be modelled based on amounts of a chemical compound in soil samples taken at two or more known time periods. Specifically, an age of an underground space may be modelled by: (1) taking soil samples from a plurality of surface locations within an underground space at two or more known periods of time; (2) taking at least one baseline soil sample at a location remote from the underground space; (3) analyzing the soil samples (including the baseline soil sample(s)) to determine an amount of a chemical compound for each soil sample; and (4) analyzing the amounts of the chemical compound determined from the soil samples taken at two or more known periods of time and the amount(s) of the chemical compound determined from the baseline soil sample(s) to determine one or more relationships based on amounts of the chemical compound measured in a plurality of soil samples taken over a period of time.

Taking Soil Samples from a Plurality of Surface Locations at Two or More Known Periods of Time: Soil samples may be taken from at least two different surface locations within an underground space and from at least two different points in time. For example, two or more samples can be taken at three different locations: a floor surface location, a ceiling surface location, and a wall surface location. Additionally, the two or more samples may be obtained from a single depth within an underground space. A "depth within an underground space" refers to a horizontal depth at which samples are taken relative to a predetermined location such as an entrance or opening of the underground space. (The vertical depth of an underground space relative to a ground surface is a different measurement).

Ideally, the two or more known time periods should be one year or more apart. In some embodiments, the two or more known time periods may be more than 2 years apart, more than 3 years apart, more than 4 years apart, more than 5 years apart, more than 8 years apart, or more than 10 years apart. In some embodiments, the two or more known time periods may be less than 15 years apart, less than 10 years apart, less than 8 years apart, less than 5 years apart, or less than 4 years apart.

Various sampling methods and tools may be used to obtain robust soil samples from the two or more surface locations within an underground space. For example, a geological coring tool may be used to extract one or more soil samples from a wall, ceiling, and/or floor surface of an underground space. The soil sample obtained by the geological coring tool may be cubic, cylindrical, or any other suitable three-dimensional shape. In some embodiments, the soil samples taken from an underground space do not need to all be the same geometry.

Further, FIG. 4A shows various possible locations for taking soil samples within an underground space. Specifically, FIG. 4A provides diagram 400 that shows a front view of a tunnel. Diagram 400 includes ceiling soil sample 416 cut from ceiling surface location 408, wall soil sample 410 cut from wall surface location 404, wall soil sample 412 cut from an opposite wall surface location, and floor soil sample 414 cut from floor surface location 406.

Taking a Baseline Soil Sample from a Remote Location: An average value of calcium carbonate under stable conditions (without underground construction) can vary in different geographical locations. For example, geological variations including average rainfall, average temperature, type of soil, depth of underground space, etc. all have an effect on an average amount of calcium carbonate in the soil. Further, as described above, construction of an underground space, such as a tunnel, can disturb the natural downward water flow and the steady precipitation and dissolution of calcium carbonate. Accordingly, a baseline sample provides insight into an average amount of calcium carbonate for a specific geographic location.

A baseline soil sample may be obtained at a location remote from the underground space where the water flow remains undisturbed. At least two methods of taking a baseline soil sample to determine a baseline calcium carbonate value are shown in FIG. 4A. For example, baseline location 418 represents a baseline sample taken at a vertical depth from the ground surface similar to an average vertical depth from the ground surface of tunnel 402, but remote from tunnel 402 so as to not be affected by the water perturbations caused by the underground construction. A baseline sample may also be calculated from soil sample slices located from wall soil sample 410 or wall soil sample 412. Specifically, a baseline calcium carbonate value can be calculated from soil sample slices located furthest away from wall surface location 404. (Soil sample slices are described in further detail below).

In some embodiments, a baseline calcium carbonate value can be subtracted from the various calcium carbonate amounts measured in the floor, ceiling, and wall soil samples, yielding an excess calcium carbonate amount. Accordingly, this excess calcium carbonate amount may be used during data analysis to account for variations between baseline calcium carbonate levels due to geological and geographical differences from one underground space to the next.

Analyzing Soil Samples to Determine an Amount of a Chemical Compound for Each Soil Sample: The soil samples may be prepared for analysis depending on the method of analysis utilized. For example, preparation may include slicing the soil samples and grinding the sample slices to a powder. Analysis may include identification and quantification of one or more chemical compound in the soil samples.

A single soil sample can be cut into several pieces. In some embodiments, a single soil sample may be cut into several slices, wherein each slice is representative of a different depth from the tunnel surface (wall, floor, or ceiling), as illustrated in FIG. 4B. The soil samples may be sliced using a geological rock saw or another suitable sawing tool. Each slice may be weighed and stored separately.

Once sliced, the slices of the soil sample(s) may be ground to a powder. For example, each slice of a soil sample may be crushed or ground individually to a coarse powder using a hammer, lab crusher, pill press, or another suitable grinding or crushing tool. The coarse powder of each individual soil sample slice may be dried in a lab vacuum oven or vacuum dryer at room temperature. For example, the coarse powder of each individual soil sample slice can be dried as required by the specific chemical analysis instrument used.

Each sample of coarse powder (from each soil sample slice) may be individually ground to a fine powder. A ball milling machine, pill press, or another suitable laboratory grinding or powdering machine may be used to grind the coarse powder to a fine powder. (In some embodiments, some components of the soil sample(s) may not be soft enough to break down to a smaller particle size. Thus, not all of the coarse powder may be capable of breaking down to a fine powder.)

The fine powder product may comprise an average particle size as required by the specific analysis technique. For example, x-ray diffraction, chemical infrared spectroscopy, x-ray fluorescence, chemical titration, or any other suitable chemical analysis techniques that can isolate the desired chemical compound and determine its bulk density in the soil sample may be used. For example, another method of chemical analysis that may be used is a method whereby the desired chemical compound is dissolved from the soil sample, and the remaining weight of the soil sample is measured to determine how much of the desired chemical compound was in the soil sample.

In some embodiments, x-ray diffraction may be used to analyze the soil samples. For an x-ray diffraction machine specifying a #100 mesh size, the coarse powder may be ground using a #140 mesh sieve (to separate out particles <106 µm) or a #100 mesh sieve (to separate out particles <150 µm). Any larger particles not soft enough to break down to a smaller particle size can be separated by an appropriate sieve. Sieved fine powder and unsieved coarse powder can be weighed separately. The sieved fine powder may be mixed thoroughly prior to x-ray diffraction. Further, it may not be possible to grind all the soil contents to a particle/mesh size necessary for the x-ray diffraction machine, and some unsieved powder may be separated out. However, calcium carbonate is a relatively soft material. Thus, under circumstances where part of the soil sample is incapable of being ground to the necessary particle/mesh size, it may reasonably be assumed that all calcium carbonate of the original soil sample slice is contained within the fine powder generated for x-ray diffraction. (Testing has shown that less than 1%, or a nominal amount of calcium carbonate from the original soil sample slice remained in the coarse unsieved powder). Accordingly, the weight-percent measurements obtained from the x-ray diffraction instrument may be corrected to account for any coarse, unsieved soil material not ground into the fine powder (as described above).

Each individual fine powder sample may be measured using an x-ray diffraction machine (or other chemical analysis process) to determine percent by weight of calcium carbonate. Analysis software such as "Terra XRD", "XPowder", or any other suitable analysis software and/or x-ray diffraction machines may be used. The weight-percent values calculated with the x-ray diffraction process may be converted to mol/m$^3$ (moles of calcium carbonate per cubic meter of soil). Once amounts of calcium carbonate have been measured for each soil sample and/or soil sample slice, relationships based on the amounts of calcium carbonate measured from a plurality of soil samples taken over a period of time may be developed.

Analyzing the Amounts of the Chemical Compound from Soil Samples to Determine Relationships Based on Amounts of the Chemical Compound Measured in a Plurality of Soil Samples Taken Over a Period of Time: The amounts of calcium carbonate from the soil samples taken from a plurality of surface locations at two or more known periods of time may be used to generate one or more relationships. Specifically, one or more rate equations may be determined from the amounts of calcium carbonate obtained from the soil samples. A rate equation may be determined for each different surface location.

One or more rate equations can be determined using the amounts of calcium carbonate determined above. For example, once the calcium carbonate levels for each slice in a soil sample have been determined, the total excess calcium carbonate for each soil sample can be summed. The total excess calcium carbonate may be equal to the baseline calcium carbonate amount determined from the baseline soil sample subtracted from the total calcium carbonate of that soil sample. In some embodiments, a baseline calcium carbonate amount may not be accounted for in a rate equation, and/or the baseline calcium carbonate amount may be accounted for at a different step of a method provided.

Determining a rate equation may comprise taking at least two soil samples obtained from the same surface location of the same underground space at two different points in time. Each of these soil samples may be analyzed to determine an amount of calcium carbonate (and optionally an excess amount of calcium carbonate above the baseline amount, as described above). With at least two data points, a rate equation for calcium carbonate deposition at a given surface location can be determined. On a graph of excess (or deficiency) compared to the baseline amount of a chemical compound (for example, calcium carbonate), the point at which the rate equation crosses the x-axis is the time at which construction on the underground space began since that is when the accumulation of the chemical compound began to diverge from the baseline value.

In some embodiments, a rate equation may be determined for soil collected from each surface location in an underground space (i.e., a wall surface location, a ceiling surface location, and/or a floor surface location). For example, two or more soil samples from the same wall location (of the same underground space) should be obtained at different points in time (ideally months or years apart) to determine a rate equation for a wall surface location. The same can be completed for a ceiling surface location and a floor surface location of the same underground space.

A rate equation for the average excess calcium carbonate accumulation at a floor surface location in an underground space may be calculated by establishing an equation that fits the curve of the data. One such example rate curve is shown below, where x=time (sec) and y=amount of calcium carbonate (mol) above the baseline value:

$$y(t)=(-3\times10^{-19})x^2+(7\times10^{-10})x-(7\times10^{-16})$$

Figure 5:
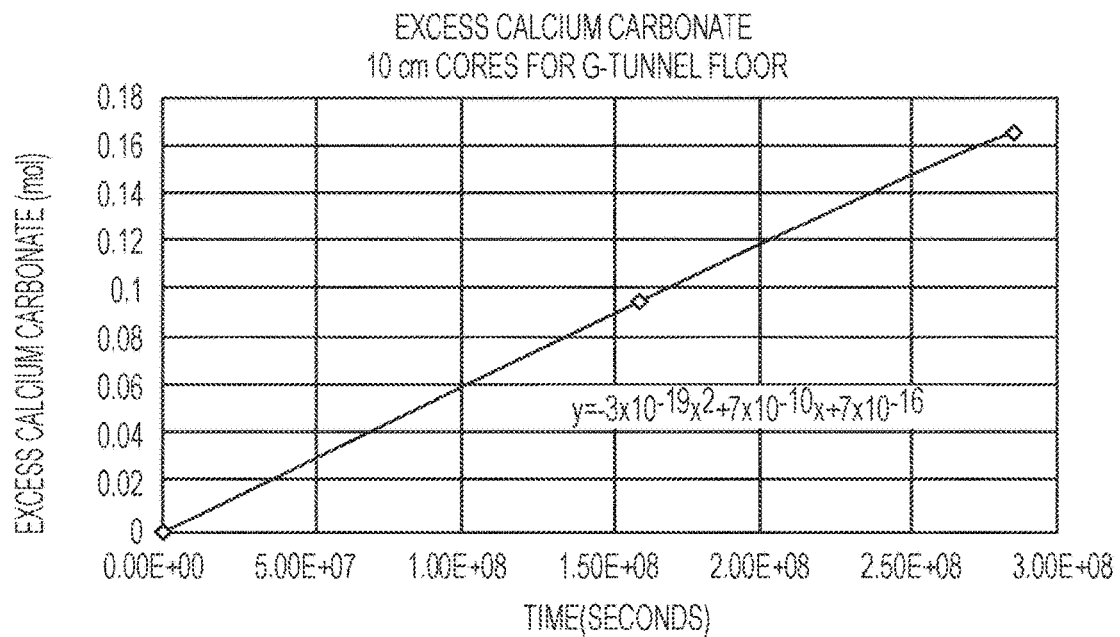
FIG. 5 graph of the rate equation for calcium carbonate in a soil sample obtained from a floor surface of an underground space.
Figure 6:
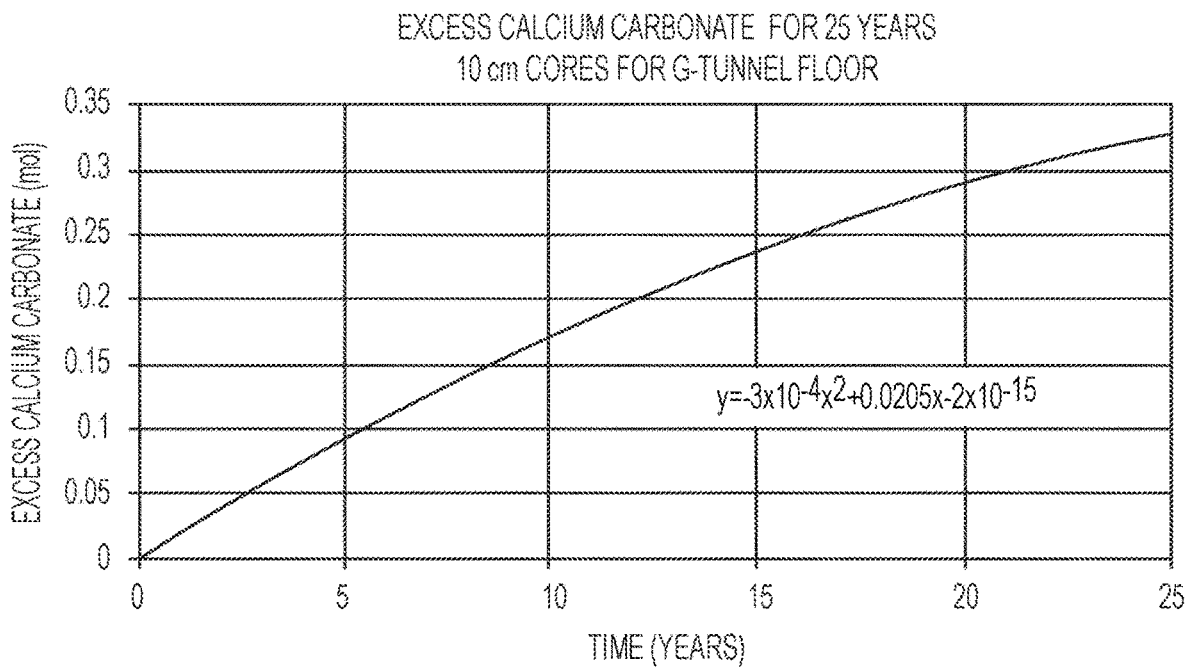
FIG. 6 is a graph of the rate equation for calcium carbonate in a soil sample obtained from a floor surface of an underground space extrapolated over a time period of 25 years.

FIG. 5 plots the above rate equation for two soil samples obtained approximately four years apart from a floor surface location. Because the quadratic coefficient ($-3\times10^{-19}$) is so close to zero, the curve of this equation begins almost linearly, as shown in FIG. 5. FIG. 6 shows the calcium carbonate deposition rate plotted over a period of 25 years. The decrease in calcium carbonate deposition rate as the curve extends away from the y-axis may be due to depletion of available calcium ions and/or carbonate ions, for example. Calcium carbonate deposition rates may also decrease based on the amount of carbon dioxide that can be released into the air, potential calcium carbonate supersaturation, and/or amounts of dissolved organic carbon that inhibit crystal growth.

As noted above, a rate equation may be determined for soil collected near each surface location in an underground space. For example, in addition to a floor surface location, rate equations may also be generated at least for a wall surface location and a ceiling surface location. As expected, the calcium carbonate deposition rates for each location will vary significantly based on the downward flow of water due to the "watershed effect" caused by construction of an underground space. In one example, calcium carbonate deposition rates for soil in a wall location and a ceiling location are plotted in FIGS. 7 and 8 respectively, and the rate equations are as follows, where x=time (sec) and y=amount of calcium carbonate (mol):

$$\text{Wall location: } y(t)=(6\times10^{-20})x^2+(9\times10^{-11})x+(1\times10^{-16})$$

$$\text{Ceiling location: } y(t)=(3\times10^{-18})x^2-(2\times10^{-10})x+(6\times10^{-16})$$

Figure 7:
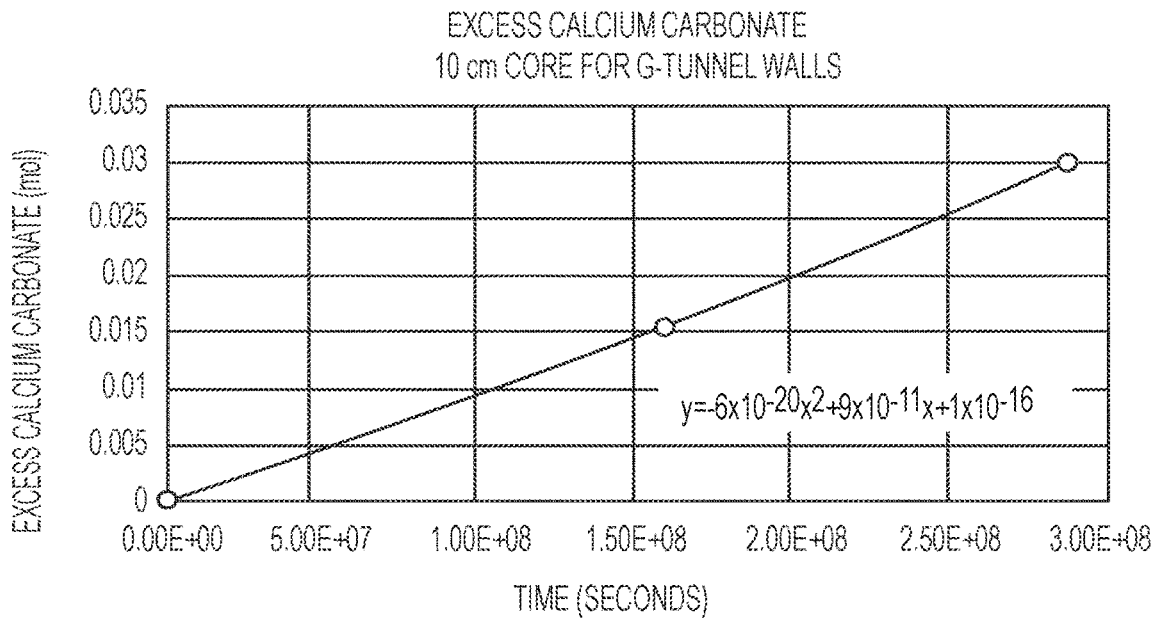
FIG. 7 is a graph of the rate equation for calcium carbonate in a soil sample obtained from a wall surface of an underground space.
Figure 8:
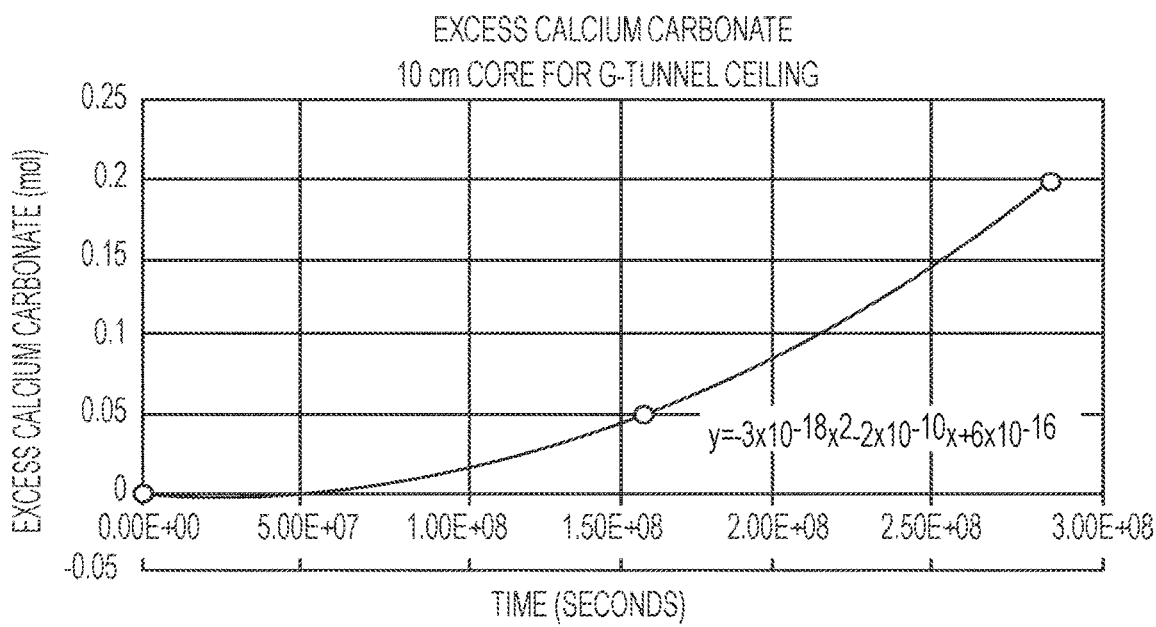
FIG. 8 is a graph of the rate equation for calcium carbonate in a soil sample obtained from a ceiling surface of an underground space.

FIGS. 5, 7, and 8 each show results from one of three rate equations (one for each of a wall surface location, a floor surface location, and a ceiling surface location). These rate equations represent the behavior of calcium carbonate deposition in soil surrounding some underground spaces. A behavior model comprising the rate equations for each of the three surface locations may be used to analyze soil samples obtained from one or more underground spaces and to determine an approximate age of an underground space.

In some embodiments, rate equations may be used to generate a model that minimizes the effect of geographic-based and geologic-based variables. For example, ratios of the wall, floor, and ceiling calcium carbonate deposition rate equations can help minimize any dependency on such variables. FIG. 3 provides a graph of the calcium carbonate rate equations to use as a model for determining the age of underground spaces. Specifically, once data from an underground space is obtained, ratios of the ceiling:floor calcium carbonate amounts, floor:wall calcium carbonate amounts, and ceiling:wall calcium carbonate amounts may be plotted along the curves to determine an age of the underground space. Further, taking ratios of calcium carbonate amounts can account for soil samples of different geometries, so long as the soil volume is consistent.

Generally, the ceiling:wall rate equation ratios will likely provide the most accurate estimates, particularly in cases when the history of the underground space is unknown. For example, the underground space may have flooded for a period of time, which may cause irregular calcium carbonate data from a floor sample. Thus, rate equation ratios that include a rate equation obtained from floor soil samples may be less accurate than a ceiling:wall ratio calcium carbonate amount ratio. Further, any calcium carbonate amount ratios that have implausible or otherwise extreme values should be considered outliers and eliminated from analysis. For example, any calcium carbonate amount ratios that are beyond the values of the graph provided in FIG. 3 may be considered outliers. As such, excluding flawed data from analysis may be expected. For example, some flawed soil samples may have been cut near unknown water flow obstructions (i.e., rocks, clay beds, along soil seepage cracks, etc.) that would disturb the gradual calcium carbonate deposition.

Further, the model(s) generated by the methods described above may be applicable within a certain time period. For example, the calcium carbonate deposition in underground spaces within the first two years of construction is often unstable due to water seepage from freshly cut walls and ceilings. Thus, the method for determining the age of the underground space according to methods disclosed herein may be unreliable for underground spaces less than two years old.

Additionally, the rate equations provided herein may only be applicable to underground spaces of certain size (height and/or width), certain vertical depth from a ground surface, etc. For example, the calcium carbonate deposition models described were generated from underground tunnels approximately one meter in width. Water flow around tunnels significantly wider or significantly narrower may experience more of an "umbrella effect", wherein the downward flowing groundwater may gather and disperse similar to the shape of an umbrella. The calcium carbonate profiles of such tunnels or other underground spaces may be different for such underground spaces than that which is disclosed herein, since the downward flow of water around underground spaces disclosed herein flows according to a "watershed effect", explained above. Accordingly, different calcium carbonate deposition rate equations may need to be developed for an underground space of a significantly different height, width, etc. than the underground spaces provided.

Determining the Age of a Tunnel Using the Model

The model described above can be used to estimate the age for any of a variety of underground spaces. Specifically, the age of an underground space may be determined by: (1) taking soil samples from a plurality of surface locations within an underground space; (2) analyzing the soil samples to determine an amount of a chemical compound for each soil sample; and (3) determining an age of the underground space using the amounts of chemical compound and one or more relationships (or models) based on amounts of the chemical compound measured from a plurality of soil samples taken over a period of time from a different underground space.

Taking Soil Samples from a Plurality of Surface Locations: Using a method described above for obtaining soil samples from various surface locations within an underground space, soil samples from at least two different surface locations may be taken as illustrated in FIG. 4A. For example, one or more soil sample(s) may be taken from at least two or more of: a wall surface location, a floor surface location, and/or a ceiling surface location of an underground space. Additionally, the soil samples may all be taken from the same location, distance, or horizontal depth within the underground space relative to a predetermined location (such as an opening or entrance of the underground space). For example, the soil samples may be obtained from wall surface location 404, floor surface location 406, and ceiling surface location 406 at a tunnel depth of 22 feet measured from an entrance of the tunnel.

In some embodiments, a baseline soil sample and/or a baseline calcium carbonate amount may be taken from a location remote from the underground space. Methods for taking one or more baseline soil sample are described above. For example, a baseline soil sample may be obtained by digging an entry shaft to a vertical depth similar to that of the underground space and cutting a soil sample. A baseline soil sample may also be obtained from a wall soil sample. Specifically, a baseline calcium carbonate amount may be the lowest calcium carbonate amount measured from a wall soil sample, or a baseline calcium carbonate amount may be a calcium carbonate amount measured furthest into the soil (away from the wall surface of the underground space).

Analyzing Soil Samples to Determine an Amount of a Chemical Compound for Each Soil Sample: As described above, soil samples may be prepared for analysis and analyzed to identify and quantify one or more chemical compounds in the soil sample.

In some embodiments, the soil samples may be prepared for analysis by cutting the soil samples into smaller pieces and/or grinding the smaller sample pieces to a powder. In some embodiments, the soil samples obtained from the surface locations may be cut into slices of approximately equal width, as shown in FIG. 4B. Precise measurements of each soil sample including the radius and length of the sample may be taken, as well as measurements of each individual soil sample slice including the thickness and distance of the slice from a surface of the underground space (i.e., a wall surface, a ceiling surface, or a floor surface).

In some embodiments, each individual slice sample may be coarsely ground and weighed. The coarse powder can be dried and then ground to a finer powder having an average particle size required by the specific chemical analysis machine or process. Any larger particles not soft enough to break down to a smaller particle size can be separated by a mesh size appropriate for analysis. This fine powder may be weighed, as well as the total ground sample slice (fine powder and remaining coarse powder). As described above, the desired particle/mesh size may be determined by the specific analysis process or instrument used to determine the amount of calcium carbonate in the soil sample. For example, the coarse powder may be ground and then using a #140 mesh sieve (to separate out particles <106 µm) or a #100 mesh sieve (to separate out particles <150 µm) for an X-ray diffraction machine specifying a #100 mesh size.

Once the soil samples have been prepared, each may be analyzed to identify and/or quantify one or more chemical compounds. Various chemical analysis methods may be used to determine one or more chemical compounds present in the soil samples and/or to determine amounts of the one or more chemical compounds. For example, x-ray diffraction may be used to determine the concentration of one or more of calcium carbonate, iron oxide, asphalt, and/or any other chemical compound whose relative concentration may be affected by the flow of groundwater and found in the soil samples.

Irregularly-shaped soil samples can be used and any irregularities may be accounted for during analysis. However, any irregularities do not necessarily affect the quality of the soil sample. Thus, the analysis of the soil samples may only consider a portion of the entire soil sample to account for any irregularly-shaped soil samples. The chemical compound data obtained using x-ray diffraction or other chemical analysis process and the physical measurements of the soil sample slices (width, radius, weight, etc.) can be used to determine the amount of calcium carbonate in the first 10 cm of each original soil sample.

To account for only a portion of the entire soil sample, a user can determine how many of the soil sample slices add to less than the desired length (8, 10, or 12 centimeters) by adding the width of each soil sample slice starting with the slice closest to the underground space surface and moving out towards the slice at the opposite end of the soil sample. If the sum of the widths of the soil sample slices do not add to exactly the desired length, a "partial slice" can be calculated. For example, based on a desired length of 12 cm, if the first 8 soil sample slices add to 11.35 cm, a "partial slice" of 0.65 cm can be calculated based on the calcium carbonate density of the soil sample slice located furthest from the tunnel surface. From this, the amount of excess calcium carbonate present in the entire soil sample of the 12 cm length can be determined.

Once the excess calcium carbonate has been calculated for soil near each of the surface locations sampled, ratios of the measurements may be calculated and plotted along the rate equations to determine an estimated age of the underground space, described below.

Determining an Age of the Underground Space: The amount of calcium carbonate in each soil sample slice and/or soil sample may be used to determine the age of the underground space from which the samples were obtained. In some embodiments, excess calcium carbonate amounts may be used. An excess calcium carbonate amount may be calculated by subtracting the baseline calcium carbonate amount from the total calcium carbonate amount. To correspond to the model described above, ratios of the excess calcium carbonate may be calculated. Specifically, the ratios of ceiling:floor, floor:wall, and ceiling:wall may be calculated and plotted on the curves of the graph provided in FIG. 3.

The ratios calculated may be plotted on the corresponding curve. For example, if a ceiling:floor calcium carbonate amount ratio is calculated, then it may be plotted on the ratio curve calculated by taking the ratio of the ceiling rate equation to the floor rate equation. Similarly, a floor:wall calcium carbonate amount ratio may be calculated and plotted on the floor:wall rate equation ratio curve, and a ceiling:wall carbonate amount ratio may be calculated and plotted on the ceiling:wall rate equation ratio curve of FIG. 3.

When plotted, the data points may all cluster together on the graph. The curve equations may be used to calculate the x-axis coordinate for the plotted ratios. These x-axis coordinates may be averaged to calculate an approximate age of the underground space in years. Any plotted data point outside of the cluster may be considered an outlier and excluded from analysis.

Below are some examples using the disclosed methods to determine the approximate age of three different underground spaces.

EXAMPLES

Example 1

Methods provided above were applied to Tunnel A. Tunnel A is located in a geographic area that receives rainfall particularly in the summer months and experiences average temperatures, both of which are conducive to calcium carbonate deposition.

Three soil samples were taken from a single tunnel depth of 22 feet relative to the tunnel entrance using a geological coring tool. One soil sample was taken vertically from a central ceiling location; one soil sample was taken horizontally from a central wall location; and one soil sample was taken vertically from a central floor location. The soil samples were cylindrical in shape and measured approximately 1.6 inches in diameter and 10 cm in length.

The soil samples were cut into round slices approximately 1 cm in thickness. Precise measurements of each soil sample including the radius and length of the soil sample were taken, as well as measurements of each individual soil sample slice including the thickness and distance of the slice from the tunnel surface (the wall surface, the ceiling surface, or the floor surface) were taken.

Each individual soil sample slice was coarsely ground and weighed. The coarse powder was dried and ground to a finer powder having an average particle size required by the specific x-ray diffraction machine or analysis process. The fine powder was then weighed. The fine powder in addition to any remaining coarse powder (that could not be ground) was weighed. The example data for each individual soil sample slice, including the data obtained from x-ray diffraction, is provided below in Table 1.

TABLE 1

| | A | B | C | D | E | F | G | H | I | J | K | L | M | N |
|---|---|---|---|---|---|---|---|---|---|---|---|---|---|---|
| 1 | | | | | Tunnel-A, East Wall (Soil Sample #2), 22 Feet, XRD Data | | | | | | | | | |
| 2 | Soil Sample Information | Slice Code | | Slice Center Depth (cm) | % W Calcite-Fine Xtal-A | g-Fine | g-Slice | g-Calcite (Xtal-A) | Slice Th (cm) | Slice Vol ($m^3$) | Density ($g/m^3$) | Calcite ($g/m^3$) | Calcite ($mol/m^3$) | Excess (mol) |
| 3 | East Side Soil | 2-DHS-01-01 | | 0.65 | 5.60 | 12.42 | 23.77 | 0.70 | 1.3 | 1.68E−05 | 1.41E+06 | 4.13E+04 | 413.11 | 6.15E−03 |
| 4 | Sample, 22' 11" | 2-DHS-02-01 | | 2.2 | 5.80 | 11.61 | 23.89 | 0.67 | 1.2 | 1.55E−05 | 1.54E+06 | 4.34E+04 | 433.29 | 5.99E−03 |
| 5 | from the | 2-DHS-03-01 | | 3.725 | 4.50 | 11.88 | 24.85 | 0.53 | 1.45 | 1.88E−05 | 1.32E+06 | 2.85E+04 | 284.68 | 4.45E−03 |
| 6 | entrance, Position | 2-DHS-04-01 | | 5.3 | 4.50 | 11.88 | 23.28 | 0.53 | 1.4 | 1.81E−05 | 1.29E+06 | 2.95E+04 | 294.85 | 4.48E−03 |
| 7 | 3. Soil sample | 2-DH5-05-01 | | 6.85 | 3.60 | 11.48 | 25.13 | 0.41 | 1.3 | 1.68E−05 | 1.49E+06 | 2.46E+04 | 245.47 | 3.33E−03 |
| 8 | was in good | 2-DHS-06-01 | | 8.5 | 2.10 | 12.69 | 25.93 | 0.27 | 1.4 | 1.81E−05 | 1.43E+06 | 1.47E+04 | 146.98 | 1.80E−03 |
| 9 | condition | 2-DHS- | | 10.1 | 2.20 | 13.27 | 25.97 | 0.29 | 1.4 | 1.81E−05 | 1.43E+06 | 1.61E+04 | 161.02 | 2.06E−03 |

TABLE 1-continued

| | A | B | C | D | E | F | G | H | I | J | K | L | M | N |
|---|---|---|---|---|---|---|---|---|---|---|---|---|---|---|
| 10 | | 07-01 2-DHS-08-01 | | 11.775 | 2.10 | 10.35 | 22.04 | 0.22 | 1.15 | 1.49E−05 | 1.48E+06 | 1.46E+04 | 145.94 | 1.47−E03 |
| 11 | | 2-DHS-09-01 | | 13.175 | 2.00 | 7.08 | 12.61 | 0.14 | 1.05 | 1.36E−05 | 9.28E+06 | 1.04E+04 | 104.13 | 7.70−E04 |
| 12 | | 2-DHS-10-01 | | 13.45 | 1.90 | 3.76 | 6.35 | 0.07 | 0.5 | 6.47E−06 | 9.81E+05 | 1.10E+04 | 110.32 | 4.07−E04 |
| 13 | Soil Sample Radius (cm) | 2.03 | | | | | | | 0.55 | 7.12E−06 | 9.81E+05 | 1.46E+04 | 145.94 | 7.01−E04 |
| 14 | Calcite Baseline Density (mol/m³) | 47.48 | | | | | | Thickness Sum | 12.15 | | | Excess Calcium Carbonate (mol) | | 2.90E−02 |
| 15 | Calcite Density (g/mol) | 100.0869 | | | | | | Thickness Sum ≤ 10 cm | 9.45 | | | Excess Calcium Carbonate (g) | | 2.90 |

Row 1 provides information about the location from which the soil sample was taken. This specific soil sample was obtained from the east wall of Tunnel A at a horizontal depth of 22 feet relative to the tunnel entrance. Additional tunnel information is provided in Column A. Column D shows the distance (cm) between the center of the soil sample slice and the tunnel surface (in this case, the east wall). Column E shows the calcium carbonate concentration (wt %) of the fine powder measured from the x-ray diffraction instrument. Column F provides the weight (g) of the fine powder; Column G shows the weight (g) of all the powder (including the fine powder and any coarse powder that did not break down to the fine powder). Column H shows the weight (g) of calcium carbonate in the soil sample slice. This calculation assumes that all the calcium carbonate is in the fine powder, and no calcium carbonate is in the coarse powder. (Calcium carbonate is a relatively soft compound and easily lends itself to being ground to a fine powder.) The slice thickness (cm) is provided in Column I. Column J shows the slice volume ($m^3$), Column K shows the slice density ($g/m^3$), Column L shows the calcium carbonate density per bulk slice volume ($g/m^3$), Column M shows calcium carbonate density per bulk slice volume ($g/m^3$), and Column N shows the excess calcium carbonate for each soil sample slice (mol). The excess calcium carbonate calculation subtracts an amount of calcium carbonate in a comparable size slice of baseline soil from the sample slice based on the baseline calcium carbonate density.

As mentioned above, soil samples may be inconsistent in size and shape. For example, pockets of loose soil may be present in the geological coring tool upon taking a sample due to expected soil irregularities. Thus, only the first 10 cm of the soil samples were analyzed to account for this possibility of irregular soil samples.

Table 1 also provides calculations for determining soil samples of exactly 10 cm in length. Field 114 provides the sum of all soil sample slice thicknesses (cm). Field 115 provides the sum of all soil sample slice thicknesses that sum to less than 10 cm (cm). In this case, the first nine slices of the soil sample sum to less than 10 cm (9.45 cm). A partial soil sample comprising 0.55 cm in width/thickness (Field 113) was added to obtain a soil sample exactly 10 cm in length. Using the density of the last slice in the soil sample (here, the tenth slice), the calcium carbonate for this partial slice was calculated to be 145.94 mol/$m^3$, and the excess calcium carbonate was 7.01×10$^{-4}$ mol. Field N14 shows the excess calcium carbonate for the total 10 cm soil sample. Specifically, Field N14 shows the excess calcium carbonate (mol) for the slices of the soil sample adding to less than 10 cm (the first nine slices adding to 9.45 cm) plus the partial (0.55 cm) slice.

For slices that may not contain 10 cm of soil sample to begin with, an imaginary "partial" slice can be calculated, much like the partial 0.55 cm slice calculated above. However, in this case, the density of any additional partial slices should be the density of the last full soil sample slice in the soil sample (the slice furthest away from the tunnel surface).

A spreadsheet like that shown in Table 1 can be calculated for each soil sample obtained from the tunnel.

To obtain a baseline soil sample, a vertical shaft was dug to the same depth as the tunnel and a baseline soil sample was extracted from a wall surface of the vertical shaft. Further, the baseline soil sample obtained from a vertical shaft was taken from a location at the same depth as the tunnel walls, nearby, but separate from the tunnel and from newly cut soil not previously exposed to weather or water perturbations caused by the tunnel excavation. To determine a baseline calcium carbonate amount, the x-ray diffraction measurement of calcium carbonate in fine powder ground from the soil sample slices. This baseline measurement was found to be comparable to soil in wall samples that were farthest from the wall surface.

Once the calcium carbonate amounts for the soil sample slices have been calculated from soil samples obtained from different tunnel surfaces (wall, floor, and/or ceiling) at the same tunnel depth (e.g., 22 ft from the tunnel entrance), the age of the tunnel can be determined. The ratios of rate equations of each of the wall, floor, and ceiling rate equations evolve smoothly based on how the fractional separation of water flow around the tunnel evolves with time. By calculating and plotting ratios of calcium carbonate to reduce the effects of variables that are different at different locations, variations in the magnitude of calcium carbonate from one underground space location to the next underground space location can be accounted for.

For example, the excess calcium carbonate for the first 10 cm of each of the soil samples (as calculated in Table 1, for example) were aggregated as shown in Table 2, below.

TABLE 2

Excess Calcium Carbonate in 10 cm Comparable Soil Samples

| Soil Sample | Excess Calcium Carbonate (mol) |
|---|---|
| Soil Sample #1, East wall, 22' | 3.02E−02 |
| Soil Sample #2, East wall, 22' | 2.90E−02 |
| Soil Sample #3, West wall, 22' | 3.13E−02 |
| Soil Sample #4, Ceiling, 22' | 1.99E−01 |
| Soil Sample #5, Floor, 22' | 1.65E−01 |

Ratios including ceiling:wall, ceiling:floor, and floor:wall were calculated (provided in Table 3) and plotted on the same graph as the rate equation ratios developed above.

TABLE 3

Ratio Analysis of Comparable Soil Samples

| Ceiling/Wall Ratio | Ceiling/Wall Ratio | Floor/Wall Ratio |
|---|---|---|
| Soil Sample #4/ 6.60E+00 Soil Sample #1 | Soil Sample #4/ 1.20E+00 Soil Sample #5 | Soil Sample #5/ 5.48E−00 Soil Sample #1 |
| Soil Sample #4/ 6.87E+00 Soil Sample #2 | | Soil Sample #5/ 5.70E−00 Soil Sample #2 |
| Soil Sample #4/ 6.35E+00 Soil Sample #3 | | Soil Sample #5/ 5.27E−00 Soil Sample #3 |

Figure 9:
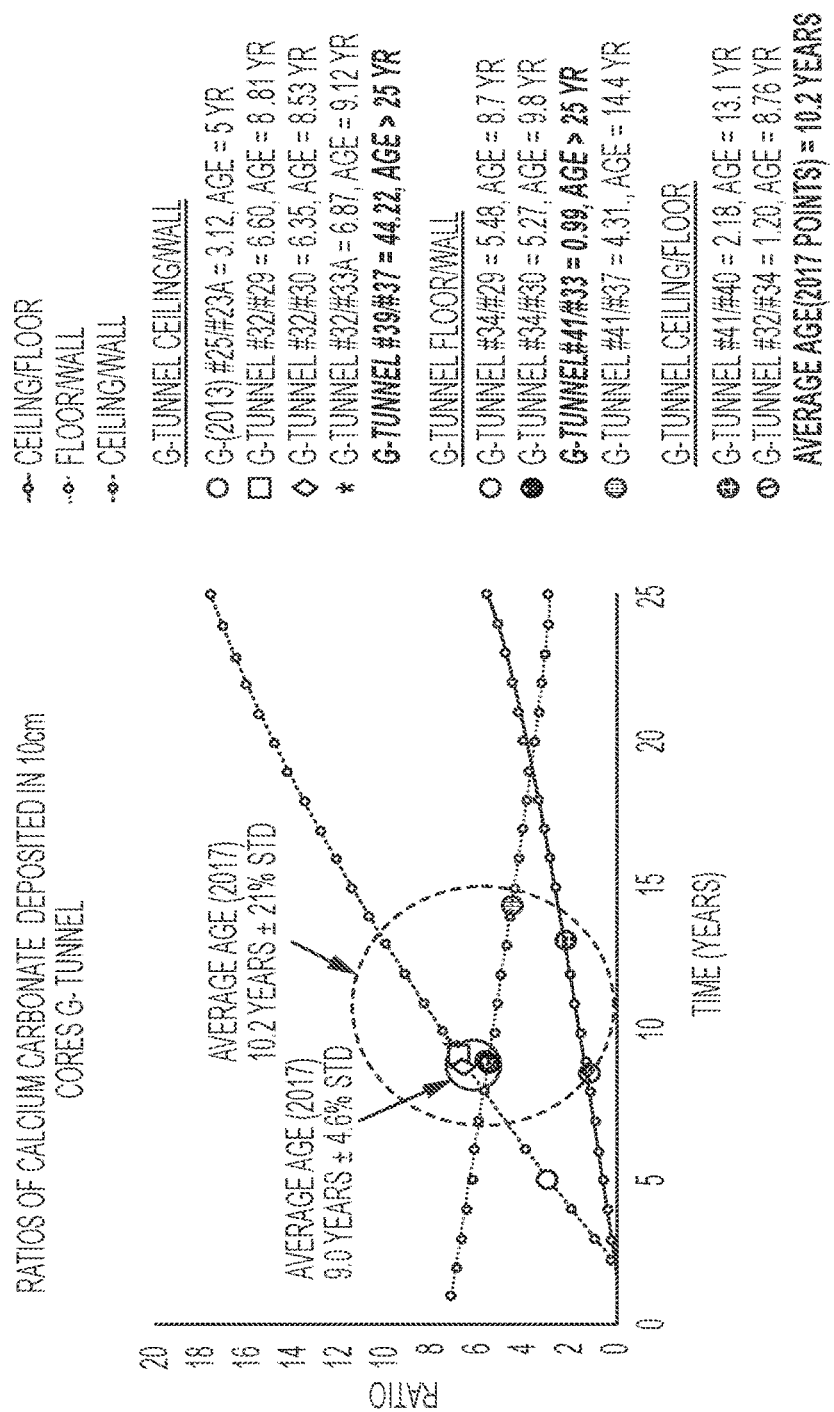
FIG. 9 is a graph of calcium carbonate ratios plotted along the rate equation ratios according to some embodiments.

As shown in FIG. 9, the ratio values were plotted on a ratio versus time (years) graph (excluding outliers). All seven ratios calculated are clustered in a similar region along the graph. The x-coordinates of each plotted ratio value can be averaged to estimate the age of the tunnel. The estimated age of the tunnel as shown in FIG. 9 is almost nine years.

Example 2

Samples from Tunnel Y were obtained and analyzed according to the method described above in Example 1. Tunnel Y is located hundreds of miles from Tunnel A in an area that has very different weather and geological characteristics. A relatively large amount of calcium carbonate was present around Tunnel Y, even with relatively low levels of water flow. However, this was because Tunnel Y is located in an area with much more calcium present in the soil than that of Tunnel A, for example.

Figure 10:
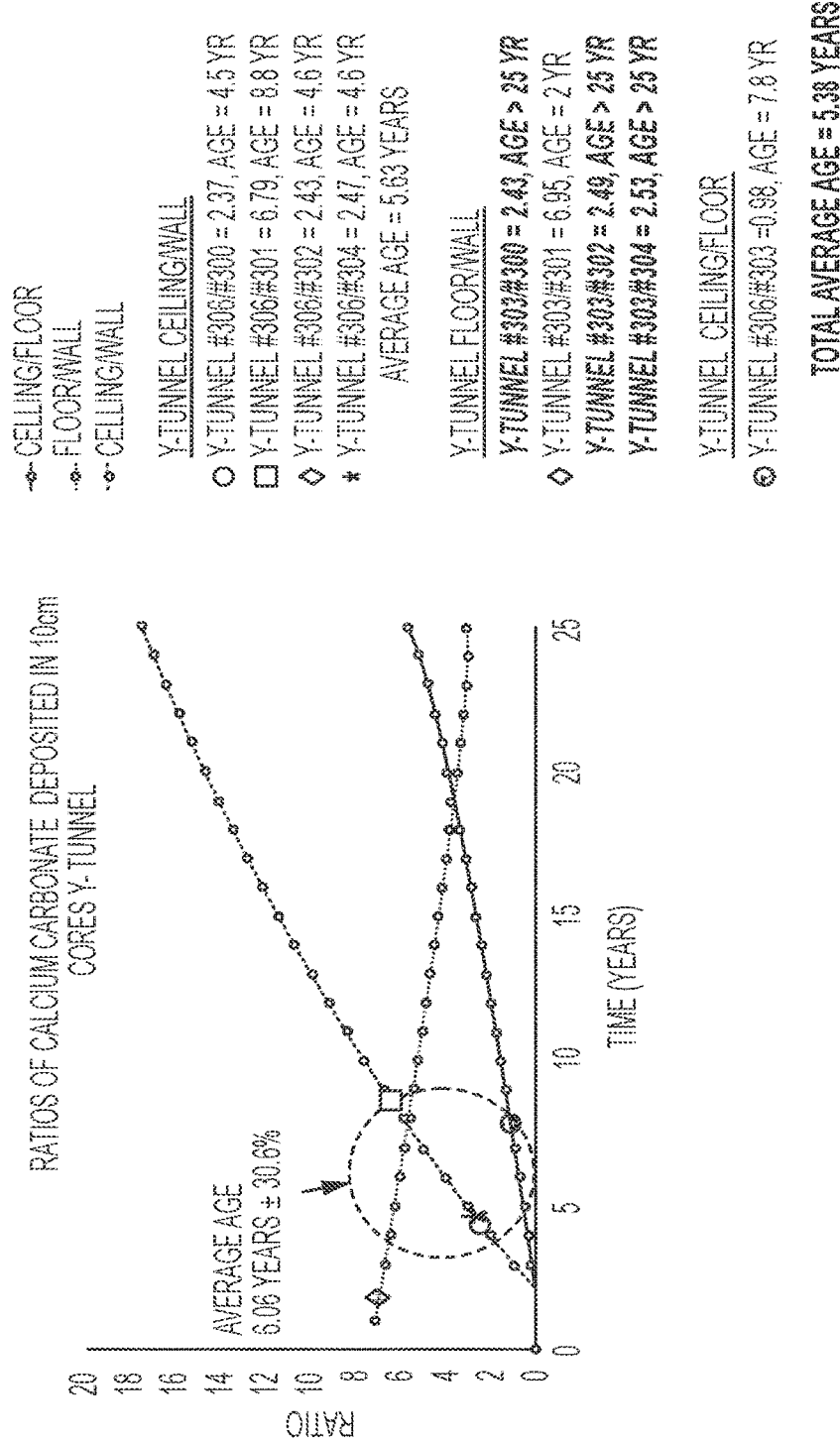
FIG. 10 is a graph of calcium carbonate ratios plotted along the wall, floor, and ceiling rate equations according to some embodiments.

As shown in FIG. 10, nine different calcium carbonate amount ratios were calculated (four ceiling:wall calcium carbonate amount ratios, four floor:wall calcium carbonate amount ratios, and one ceiling: floor calcium carbonate amount ratio). Three of the calcium carbonate amount ratios including the floor sample data were outliers, since they were beyond the values of the graph (greater than 25 years). Accordingly, of the six calcium carbonate amount ratios that were plotted on the ratio rate equations graph, the average estimated age of the tunnel was 5.38 years. However, the single remaining ratio including floor data yielded an estimated age of 2 years. If this value is also considered an outlier and removed from analysis, the average age of the remaining five calcium carbonate amount ratios is 6.06 years.

In this case, the exact age of the Tunnel Y was known, and thus the accuracy of disclosed methods were confirmed. Specifically, the exact age of the tunnel at the time the samples were obtained was 6 years and 1 month, or 6.08 years. Thus, by removing all outlier values from the average estimated age, disclosed methods were able to achieve an average estimated age of 6.06 years for Tunnel Y. Note that all outlier values included data from a floor sample, and of the data points used to determine an age of 6.06 years, only one data point (of five total) incorporated any floor data.

Example 3

Tunnel CH was tested according to methods disclosed above. Tunnel CH is characterized by a rift in geological history, wherein one side of the rift has clay soil and another side of the rift has sandy soil.

Figure 11:
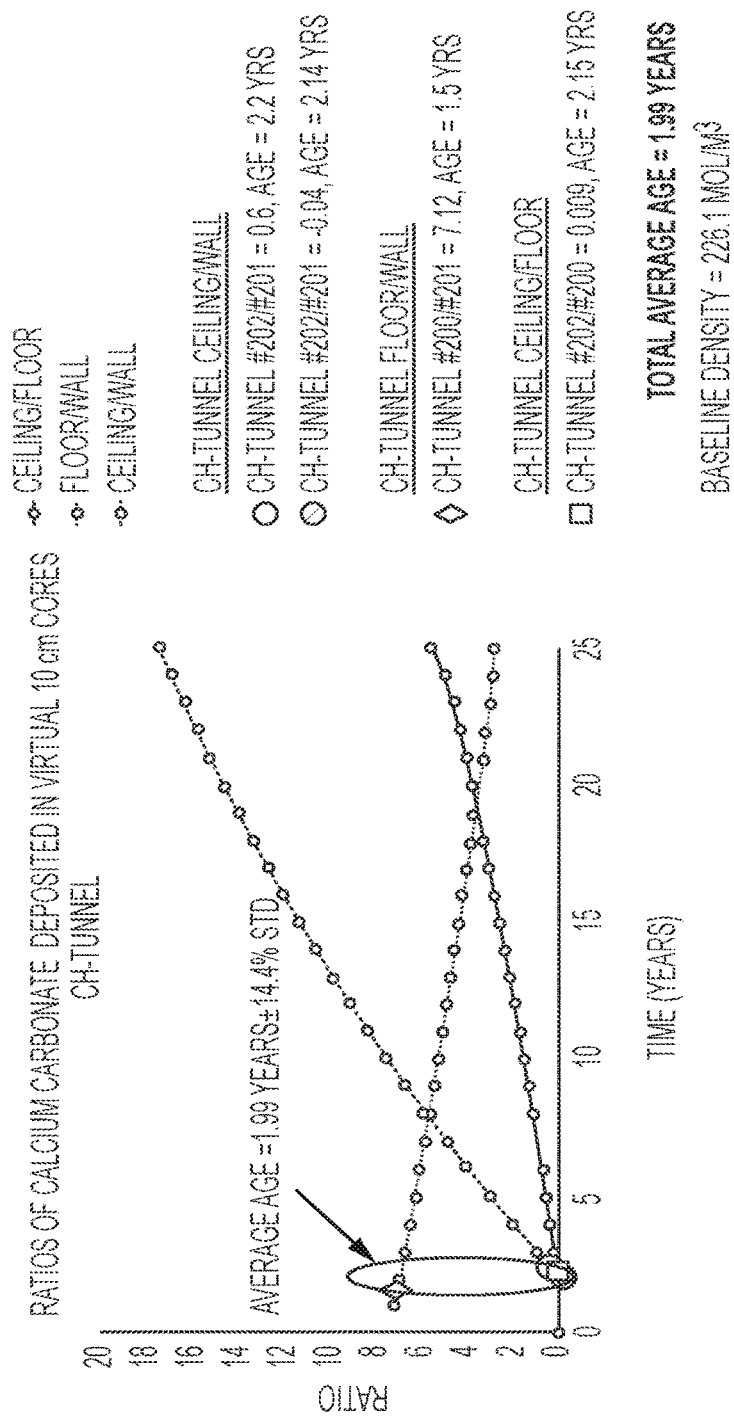
FIG. 11 is a graph of calcium carbonate ratios plotted along the wall, floor, and ceiling rate equations according to some embodiments.

Fewer samples were obtained from Tunnel CH than from Tunnels A and Y. FIG. 11 shows the calcium carbonate amount ratios plotted along the ratio rate equations. Two ceiling:wall calcium carbonate amount ratios, one floor:wall calcium carbonate amount ratio, and one ceiling:floor calcium carbonate amount ratio were calculated and plotted. As shown, the average estimated age for all four ratios was 1.99 years. Based on public records (i.e., tax records, press reports, deeds, etc.), the actual age of Tunnel CH was anywhere from 0.16 years to 1.5 years old at the time the soil samples were taken. As explained above, the calcium carbonate deposition rates around an underground space within the first two years after construction can be unstable. Accordingly, methods for determining the age of underground spaces disclosed herein can be less accurate for underground spaces less than two years of age at the time of sample extraction. Despite this instability, methods provided were still able to determine an age of Tunnel CH with reasonably accuracy.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A method for generating a model to determine the age of an underground space comprising:

analyzing soil samples collected from a plurality of surface locations within an underground space at a first and a second known periods of time to determine an amount of a chemical compound in each of the soil samples from the plurality of surface locations within the underground space from the first and second known periods of time; and determining one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

2. The method of claim 1, wherein the first and the second known periods of time are one year or more apart.

3. The method of claim 1, further comprising analyzing a soil sample from one or more locations remote from the underground space.

4. The method of claim 1, wherein the plurality of surface locations comprises two or more of a wall surface location, a floor surface location, and a ceiling surface location.

5. The method of claim 1, wherein analyzing the soil samples from the plurality of surface locations within the underground space comprises:

receiving a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder; and analyzing each individual powder sample to determine amounts of the chemical compound in each sample slice of the plurality of sample slices of the soil sample.

6. The method of claim 1, wherein determining one or more relationships between the determined amounts of the chemical compound in the soil samples comprises determining one or more ratios of a first amount of the chemical compound in a soil sample from one surface location of the plurality of surface locations within the underground space to a second amount of the chemical compound in a soil sample from a second surface location of the plurality of surface locations within the underground space.

7. The method of claim 6, wherein determining one or more relationships between the determined amounts of the chemical compound in the soil samples further comprises determining one or more ratios of the second amount of the chemical compound in the soil sample from the second surface location of the plurality of surface locations within the underground space to a third amount of the chemical compound in a soil sample from a third surface location of the plurality of surface locations within the underground space.

8. A system for generating a model to determine the age of an underground space comprising:

a processor; and a memory storing instructions that, when executed by the processor, cause the processor to:

analyze soil samples collected from a plurality of surface locations within an underground space at a first and a second known periods of time to determine an amount of a chemical compound in each of the soil samples from the plurality of surface locations within the underground space from the first and second known periods of time; and determine one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

9. The system of claim 8, wherein the first and the second known periods of time are one year or more apart.

10. The system of claim 8, wherein the instructions, when executed by the processor, further cause the processor to analyze a soil sample from one or more locations remote from the underground space.

11. The system of claim 8, wherein the plurality of surface locations comprises two or more of a wall surface location, a floor surface location, and a ceiling surface location.

12. The system of claim 8, wherein the instructions that cause the processor to analyze soil samples collected from a plurality of surface locations within the underground space comprise instructions that cause the processor to, when having received a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder, analyze each individual powder sample to determine amounts of the chemical compound in each sample slice of the plurality of sample slices of the soil sample.

13. The system of claim 8, wherein the instructions causing the processor to determine one or more relationships between the determined amounts of the chemical compound in the soil samples comprise instructions that cause the processor to determine one or more ratios of a first amount of the chemical compound in a soil sample from one surface location of the plurality of surface locations within the underground space to a second amount of the chemical compound in a soil sample from a second surface location of the plurality of surface locations within the underground space.

14. The system of claim 13, wherein the instructions that cause the processor to determine one or more relationships between the determined amounts of the chemical compound in the soil samples further comprise instructions that cause the processor to determine one or more ratios of the second amount of the chemical compound in the soil sample from the second surface location of the plurality of surface locations within the underground space to a third amount of the chemical compound in a soil sample from a third surface location of the plurality of surface locations within the underground space.

15. A non-transitory computer readable storage medium storing instructions for generating a model to determine the age of an underground space, wherein the instructions are executable by a system and a processor to cause the system to:

analyze soil samples collected from a plurality of surface locations within an underground space at a first and second known periods of time to determine an amount of a chemical compound in each of the soil samples from the plurality of surface locations within the underground space from the first and second known periods of time; and determine one or more relationships between the determined amount of the chemical compound in the soil samples from the plurality of surface locations within the underground space at the first known period of time and the determined amount of the chemical compound in the soil samples from the plurality of surface locations with the underground space at the second known period of time.

16. The non-transitory computer readable storage medium of claim 15, wherein the first and second known periods of time are one year or more apart.

17. The non-transitory computer readable storage medium of claim 15, wherein the instructions, when executed by the processor, further cause the processor to analyze a soil sample from one or more locations remote from the underground space.

18. The non-transitory computer readable storage medium of claim 15, wherein the plurality of surface locations comprises two or more of a wall surface location, a floor surface location, and a ceiling surface location.

19. The non-transitory computer readable storage medium of claim 15, wherein the instructions that cause the processor to analyze the soil samples from the plurality of surface locations within the underground space comprise instructions that further cause the processor to, when having received a soil sample that has been taken from a surface location of the plurality of surface locations and sliced into a plurality of sample slices, wherein each sample slice of the plurality of sample slices has a width of 0.5 inches to 1.5 inches, represents a different distance from the surface location of the plurality of surface locations, and has been grinded individually to a powder, analyze each individual powder sample to determine amounts of the chemical compound in each sample slice of the plurality of sample slices of the soil sample.

20. The non-transitory computer readable storage medium of claim 15, wherein the instructions that cause the processor to determine one or more relationships between the determined amounts of the chemical compound in the soil samples comprise instructions that cause the processor to determine one or more ratios of a first amount of the chemical compound in a soil sample from one surface location of the plurality of surface locations within the underground space to a second amount of the chemical compound in a soil sample from a second surface location of the plurality of surface locations within the underground space.

21. The non-transitory computer readable storage medium of claim 20, wherein the instructions that cause the processor to determine one or more relationships between the determined amounts of the chemical compound in the soil samples further comprise instructions that cause the processor to determine one or more ratios of the second amount of the chemical compound in the soil sample from the second surface location of the plurality of surface locations within the underground space to a third amount of the chemical compound in a soil sample from a third surface location of the plurality of surface locations within the underground space.

* * * * *